United States Patent [19]

Petigara et al.

[11] Patent Number: 5,068,344

[45] Date of Patent: Nov. 26, 1991

[54] PROCESS FOR THE PREPARATION OF SALT FREE, WATER FREE 3-ISOTHIAZOLONE COMPOUNDS

[75] Inventors: Ramesh B. Petigara, Hatfield; Norman A. Leister, Huntingdon Valley; Barry J. Pendell, Lansdale; Robert A. Woodruff, Buckingham, all of Pa.

[73] Assignee: Rohm and Haas Company, Philadelphia, Pa.

[21] Appl. No.: 464,472

[22] Filed: Jan. 12, 1990

[51] Int. Cl.$^5$ .......................................... C07D 275/02
[52] U.S. Cl. ..................................................... 548/213
[58] Field of Search ......................................... 548/213

[56] References Cited

U.S. PATENT DOCUMENTS

| | | | |
|---|---|---|---|
| 3,849,430 | 11/1974 | Lewis et al. | 548/213 |
| 3,870,795 | 3/1975 | Miller et al. | 548/213 |
| 4,031,055 | 6/1977 | Dupont | 524/83 |
| 4,067,878 | 1/1978 | Miller et al. | 548/213 |
| 4,129,448 | 12/1978 | Greenfield | 548/213 |
| 4,652,530 | 3/1987 | Rothman | 436/178 |
| 4,824,957 | 4/1989 | Amick | 548/213 |

FOREIGN PATENT DOCUMENTS 95907 12/1983 European Pat. Off. .

*Primary Examiner*—C. Warren Ivy
*Assistant Examiner*—Celia Chang
*Attorney, Agent, or Firm*—Michael B. Fein

[57] ABSTRACT

A process for preparing a 3-isothiazolone of the formula

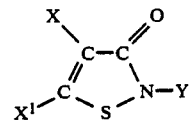

wherein
Y is selected from the group consisting of alkyl or substituted alkyl of 1 to 10 carbon atoms; unsubstituted or halogen-substituted alkenyl or alkynyl of 2 to 10 carbon atoms; and aralkyl or halogen-, lower alkyl-, or lower alkoxy-substituted aralkyl of up to 10 carbon atoms;
X is hydrogen or a ($C_1$–$C_2$) alkyl; and
$X^1$ is hydrogen, chlorine, or a ($C_1$–$C_2$) alkyl; comprising
(a) reacting anhydrous ammonia with an isothiazolone salt of the formula

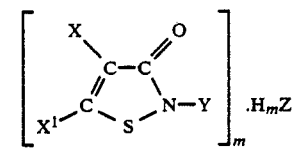

wherein
Z is chlorine, bromine, sulfate or fluorosulfonate;
m is 1 when Z is chlorine, bromine or fluorosulfonate, and m is 2 when Z is sulfate; and
(b) separating the resultant $(NH_4)_mZ$ from the resultant free base isothiazolone is disclosed.

13 Claims, No Drawings

PROCESS FOR THE PREPARATION OF SALT FREE, WATER FREE 3-ISOTHIAZOLONE COMPOUNDS

BACKGROUND OF INVENTION

1. Field of Invention

This invention concerns the manufacture of 3-isothiazolones, and in particular it is concerned with a process for preparing 3-isothiazolones containing little or no salt ("salt-free"), and also little or no water ("water-free").

2. Description of the Prior Art

3-Isothiazolones of the formula:

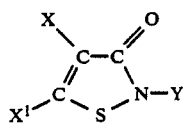

wherein Y is an alkyl or substituted alkyl of 1 to 10 carbon atoms; an unsubstituted or halogen substituted alkenyl or alkynyl of 2 to 10 carbon atoms; an aralkyl or halogen-, lower alkyl-, or lower alkoxy-substituted aralkyl of up to 10 carbon atoms; X is hydrogen or a $(C_1-C_2)$alkyl; and $X^1$ is hydrogen, chlorine, or a $(C_1-C_2)$alkyl are disclosed in U.S. Pat. Nos. 3,523,121 and 3,761,488.

These 3-isothiazolones are well known as microbicides and are employed in many industrial and household systems. Since the 3-isothiazolones in aqueous solutions are generally unstable, stabilizing divalent metal salts as described in U.S. Pat. Nos. 3,870,795 and 4,067,878 are usually incorporated.

In certain applications, e.g., preservation of latex emulsion, these metal stabilization salts cause problems which can reduce the performance or value of such systems.

Another problem with such metal stabilization salts is that they cause corrosion in certain systems. For example, chloride salts have a corrosive effect on many metals and are to be avoided where possible. In water treatment systems where low cation and anion levels are important, it is desirable to eliminate such salts. In the stabilization of plastic articles, salts may contribute to deterioration of optical properties and/or increase water pickup and haze levels.

In some cosmetic formulations, it is also important to eliminate inorganic salt, especially nitrate.

Isothiazolone hydrochloride salts (isothiazolone•HCl) are generated in the general prior art process for manufacturing isothiazolones. Such a process for the manufacture of a mixture of 5-chloro-2-methyl-3-isothiazolone and 2-methyl-3-isothiazolone is described in U.S. Pat. No. 3,849,430 and European Patent No. 95907. The isothiazolone•HCl is generated in the chlorination/cyclization step of this process during which either a di-(or tri)thiaodiamide or a mercaptoamide is cyclized:

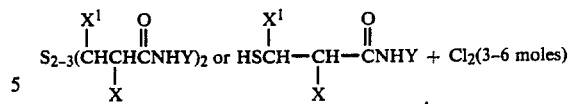

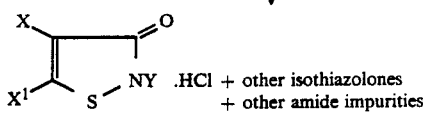

The chlorination slurry is then filtered, then the isothiazolone•HCl cake is washed and reslurried or dissolved in the same or different solvent. In aqueous systems, a neutralizing agent such as magnesium oxide or calcium oxide is then added to yield the free base isothiazolone and a chloride salt:

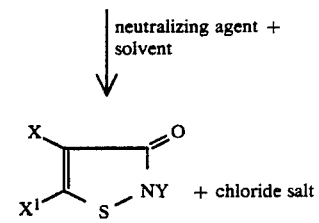

Certain organic amines have been suggested as neutralizing agents in non-aqueous organic media in U.S. Pat. No. 4,824,957. Such organic amines produce organic amine hydrohalide salts as byproduct neutralization salts. The amount of organic amine required to neutralize the isothiazolone hydrohalide salt is difficult to determine and thus the neutralization endpoint cannot be controlled precisely. Any excess organic amine remains in the organic solvent solution of the free base isothiazolone after neutralization and contaminates the final product solution, and furthermore may also chemically react with the free base isothiazolone to produce additional byproducts. In addition, these residual amines may also act as a source of nitrosamine contaminants, if such free base isothiazolone were to be formulated to aqueous solutions stabilized with nitrate salts.

The free base isothiazolone and amine hydrochloride salt (amine•HCl) which are formed from the neutralization reaction are separated by filtering off the solid salt from the solution of free base isothiazolone. However, the amine•HCl is sparingly to appreciably soluble in the solvent, and consequently the final isothiazolone product may not be entirely salt-free.

None of the prior art processes produces an isothiazolone which is substantially pure, salt-free, and water-free.

SUMMARY OF THE INVENTION

It is an object of the present invention to provide a process to produce salt free isothiazolones of high purity and in high yield. It is a further object to produce isothiazolones which are pure, salt free, and water free.

These objects and others which will become apparent from the following disclosure are achieved by the present invention which comprises in one aspect a process for preparing a 3-isothiazolone of the formula

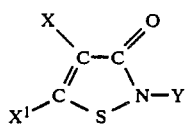

wherein
Y is selected from the group consisting of alkyl or substituted alkyl of 1 to 10 carbon atoms; unsubstituted or halogen-substituted alkenyl or alkynyl of 2 to 10 carbon atoms; and aralkyl or halogen-, lower alkyl-, or lower alkoxy-substituted aralkyl of up to 10 carbon atoms;

X is hydrogen or a ($C_1$-$C_2$)alkyl; and $X^1$ is hydrogen, chlorine, or a ($C_1$-$C_2$)alkyl; comprising (a) reacting anhydrous ammonia with an isothiazolone salt of the formula

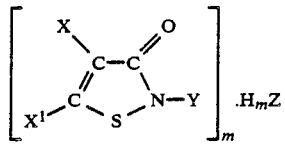

I wherein
Z is chlorine, bromine, sulfate or fluorosulfonate;
m is 1 when Z is chlorine, bromine, or fluorosulfonate and m is 2 when Z is sulfate; and (b) separating the resultant $(NH_4)_mZ$ from the resultant free base isothiazolone.

Y is preferably methyl, ethyl, propyl, isopropyl, butyl, hexyl, octyl, hydroxymethyl, chloromethyl, chloropropyl, benzyl, 4-methoxybenzyl, 4-chlorobenzyl, phenethyl, 2-(4-chlorophenyl)ethyl, 4-phenylbutyl, and the like.

Z is preferably chlorine or bromine, and most preferably chlorine.

The expressions "lower" alkyl, lower alkoxy, and the like mean that the alkyl or alkoxy portion thereof has about 1 to 2 carbon atoms.

DETAILED DESCRIPTION OF THE INVENTION AND THE PREFERRED EMBODIMENTS

The use of organic solvent in the process to dissolve or suspend the salt is optional, but is preferred.

The process of the invention comprises contacting I or I organic solvent mixture with anhydrous ammonia in an amount sufficient to neutralize the $H_mZ$ present to form free base isothiazolone and an insoluble $(NH_4)_mZ$ salt, and then separating the $(NH_4)_mZ$ salt from the mixture. The organic solvents are selected such that the free base isothiazolone is essentially soluble and the $(NH_4)_mZ$ salt is essentially insoluble therein. By the term "essentially soluble" we mean that the free base isothiazolone is sufficiently soluble in the solvents used such that >95% of the free base isothiazolone available is recovered after separation of the $(NH_4)_mZ$ salt. By the term "essentially insoluble" we mean that the $(NH_4)_mZ$ salt is sufficiently insoluble in the solvent or solvent mixture used such that <0.5% $(NH_4)_mZ$ salt is found in the isolated free base isothiazolone, and preferably <0.1%.

Preferably the solvent selected is also employed as the solvent in the preceding halogenation/cyclization step of making the I. Suitable solvents for the neutralization include alcohols, glycols, glycol ethers, aromatic hydrocarbons, chlorinated aromatic hydrocarbons, aliphatic hydrocarbons, chlorinated aliphatic hydrocarbons, and acetate esters. Acetate esters are preferred, particularly ethyl and butyl acetate.

Preferred organic solvents for dissolving or suspending the salt are selected from the group consisting of ($C_1$-$C_5$)alkyl alcohol, ($C_2$-$C_8$)alkylene glycol, ($C_3$-$C_{10}$)alkylene glycol ether, ($C_6$)aromatic hydrocarbon, ($C_1$-$C_2$)alkyl-substituted aromatic hydrocarbon, chlorosubstituted ($C_6$)aromatic hydrocarbon, chlorosubstituted ($C_1$-$C_2$)alkyl-substituted aromatic hydrocarbon, ($C_6$-$C_8$)alkane, chloro-substituted($C_1$-$C_3$)alkane, and ($C_1$-$C_4$)alkyl ester of acetic acid.

A particularly preferred group of solvents is selected from the group consisting of ethylene glycol, propylene glycol, 1,3-butanediol, dipropylene glycol, ethylene glycol butyl ether, toluene, monochlorobenzene, heptane, dichloromethane, 1,2-dichloroethane, ethyl acetate, and butyl acetate.

During the neutralization, the amount of ammonia introduced to the solution or suspension of I salt should be less than or just equal to the stoichiometric amount necessary to neutralize the salt. Excess ammonia should be avoided to prevent reacting with the free base isothiazolone, resulting in lower yields, generation of by-products giving lower purity, and high color. We have discovered that we are able to avoid excess ammonia by monitoring for ammonia in the vapor space above the neutralized I solution. We prefer to use an ammonia gas sensing probe or moist litmus paper to precisely control the amount of ammonia introduced for neutralization so that little or no excess accumulates in the free base isothiazolone solution once all of the $H_mZ$ has been neutralized.

Solvents which may be used in the isothiazolone•HZ neutralization step but not for the preceding halogentation/cyclization step are alcohol, e.g., methanol; glycols, e.g., ethylene glycol, 1,3-butanediol, dipropylene glycol, and propylene glycol; and glycol ethers, e.g., methyl and butyl ethers of ethylene glycol and diethylene glycol. The final free base isothiazolone may be formulated in these solvents, thereby eliminating the need for a solvent removal step (via vacuum stripping or distillation) after neutralization. These solvents may also be used in combination, i.e., in mixtures, with the solvents used for the halogenation/cyclization step. Depending upon the alcohol, glycol, or glycol ether selected for the neutralization, greater concentrations of $(NH_4)_mZ$ salt than desired may be found in the intermediate free base isothiazolone solutions; these $(NH_4)_mZ$ salt concentrations can be reduced to acceptable levels upon formulation of the final free base isothiazolone in selected solvents, e.g., dipropylene glycol, followed by filtration.

Other strong acid salts such as the (isothiazolone)$_2$I0S ($H_2SO_4$) or (isothiazolone)•$HFSO_3$ salts may be neutralized with anhydrous ammonia to produce the free base isothiazolone and insoluble ammonium sulfate or fluorosulfonate.

In addition to using the process of this invention to obtain highly pure salt-free water-free formulations of isothiazolones and isothiazolone mixtures, the invention may be used to obtain different ratios of two or more isothiazolones initially present in an I mixture. For example, a 3/1 mixture of (5-chloro-2-methyl-3-isothiazolone/2-methyl-3-isothiazolone)$_m$•H$_m$Z may be only partially neutralized with ammonia, followed by isolation of the free base isothiazolone (after filtering off the remaining I and (NH$_4$)$_m$Z salts). The free base isothiazolone obtained by this procedure will be enriched in 5-chloro-2-methyl-3-isothiazolone relative to 2-methyl-3-isothiazolone due to the differences in basicity of the free base isothiazolones. This enrichment procedure may be practiced with the process of this invention whenever there is difference in basicities of the isothiazolones in the initial mixture of I salts to be neutralized. Indeed, one may use the process of the invention to isolate a highly enriched 5-chloro-2-methyl-3-isothiazolone mixture from a mixture of 5-chloro-2-methyl-3-isothiazolone/2-methyl-3-isothiazolone. The remaining I may then be treated with additional ammonia to liberate the free base isothiazolone and thereby isolate a highly enriched 2-methyl-3-isothiazolone mixture.

As can be seen from the proceeding disclosure and following examples, the process of the invention provides a unique, novel, useful, and highly advantageous process of producing free base isothiazolone which is substantially free of water and free of salt. The preferred isothiazolones contain less than about 0.1% water and less than about 0.1% (NH$_4$)$_m$Z based on weight of isothiazolone.

The following examples illustrate the process of the present invention; they are illustrative only, and are not intended to limit the scope of the invention.

EXAMPLE 1

Preparation of 3:1 Mixture of 5-Chloro-2-Methyl-3-Isothiazolone and 2-Methyl-3-Isothiazolone This example illustrates using ethyl acetate as the organic solvent for both the chlorination/cyclization and neutralization and anhydrous ammonia as the neutralizing agent; the chlorination/cyclization is carried out following the process of U.S. Pat. No. 3,849,430 and European Patent 95907. The same solvent is used for both chlorination/cyclization and neutralization.

Step 1: Chlorination of N-Methyl-3-Mercaptopropionamide (MMPA)

A 1-liter jacketed kettle with a bottom take-off was equipped with an overhead agitator, a thermometer, a chlorine inlet, an inlet for a 28% solution of MMPA in ethyl acetate, and a condenser connected to a caustic scrubber. To this kettle was charged ethyl acetate. To the heel of ethyl acetate were co-fed chlorine and the 28% MMPA solution over a 1-3 hour period while maintaining good mixing and temperature control. The resultant chlorination slurry of isothiazolone•HCl salts was filtered to isolate the isothiazolone•HCl cake. The isothiazolone•HCl cake was washed thoroughly with ethyl acetate to yield a highly pure mixture of isothiazolone•HCl salts (99.9% by HPLC and HCl analyses, 73.5% 5-chloro-2-methyl-3-isothiazolone/26.5% 2-methyl-3-isothiazolone or 2.8:1 ratio).

Step 2: Neutralization of the Isothiazolone•HCl Salt

The mixture of isothiazolone•HCl salts was reslurried in fresh ethyl acetate (25% solids) and anhydrous ammonia was passed gradually through the slurry at a temperature of 10°-22° C. until free ammonia could be detected in the head space of the container by an ammonia gas sensing probe. The isothiazolone•HCl salt mixture absorbed 22.3 g of ammonia before the free ammonia was detected in the gas head space. The resultant slurry of ammonium chloride in a solution of free base isothiazolone was then filtered on a vacuum Buchner funnel and the filter cake was thoroughly washed with fresh ethyl acetate.

Step 3: Solvent Strip

The filtrate and the ethyl acetate washings were combined and stripped under reduced pressure (40° C./20 mm Hg to 50° C./2 mm Hg) to yield 176.8 g of high purity, free base isothiazolone product: 76.4% 5-chloro-2-methyl-3-isothiazolone/23.4% 2-methyl-3-isothiazolone (ratio of 3.3:1), 99.8% purity (<0.1% NH$_4$Cl). Overall yield was 84.2 mole % based on starting MMPA.

Step 4: Formulation of 5-chloro-2-methyl-3-isothiazolone/2-methyl-3-isothiazolone in Dipropylene Glycol (DPG)

The above highly pure free base isothiazolone mixture was dissolved in an appropriate amount of DPG to give 5% isothiazolone (active ingredient) in DPG solution.

The formulation containing 5% active ingredient was then added to various latex emulsions at 30-100 ppm (active ingredient) providing excellent protection against biological fouling without causing any gel formation in the latex.

EXAMPLE 2

Preparation of 3:97 Mixture of 5-Chloro-2-Methyl-3-Isothiazolone/2-Methyl-3-Isothiazolone In a manner similar to Step 1 of Example 1, an isothiazolone•HCl salt was obtained having purity of 98.2% and a 5-chloro-2-methyl-3-isothiazolone/2-methyl-3-isothiazolone ratio of 2:98.

Following the procedure of Step 2 of Example 1, the isothiazolone•HCl salt was neutralized with ammonia and the resultant free base isothiazolone was obtained in 98.2% purity (5-chloro-2-methyl-3-isothiazolone/2-methyl-3-isothiazolone ratio of 3:97, <0.1% NH$_4$Cl) and an overall molar yield of 86.4%.

EXAMPLE 3

Preparation of 92:8 Mixture of 5-Chloro-2-Methyl-3-Isothiazolone/2-Methyl-3-Isothiazolone Step 1: Chlorination of MMPA Following the procedure of Step 1 of Example 1, an isothiazolone•HCl salt sample was obtained having a 99.9% purity (91% 5-chloro-2-methyl-3-isothiazolone/9% 2-methyl-3-isothiazolone or 10.1:1 ratio) based on HPLC and HCl analyses.

Step 2: Neutralization of the isothiazolone•HCl Salt

This step was repeated as in Step 2 of Example 1 to give 181 g of the free base isothiazolone (99.5%, <0.1% NH$_4$Cl) in a ratio of 92% 5-chloro-2-methyl-3-isothiazolone/8% 2-methyl-3-isothiazolone (11.4:1). The overall isothiazolone yield based on starting MMPA was 82 mole %.

EXAMPLE 4

Preparation of 5-Chloro-2-Methyl-3-Isothiazolone/2-Methyl-3-Isothiazolone Mixtures with Toluene Solvent Step 1 of Example 1 was repeated except the ethyl acetate solvent was replaced with toluene. The isothiazolone•HCl obtained had a purity of only 89%

(5-chloro-2-methyl-3-isothiazolone/2-methyl-3-isothiazolone ratio of 3.7:1).

Following the procedure of Step 2 of Example 1, the isothiazolone•HCl salt was neutralized with ammonia to produce the free base isothiazolone in 88% purity (<0.1% NH$_4$Cl) and 5-chloro-2-methyl-3-isothiazolone/2-methyl-3-isothiazolone ratio of 4.4:1.

EXAMPLE 5

Preparation of 5-Chloro-2-Methyl-3-Isothiazolone/2-Methyl-3-Isothiazolone Mixtures Employing Butyl Acetate (BuOAc) Solvent Step 1 of Example 1 was repeated, except the ethyl acetate solvent was replaced with BuOAc. The isothiazolone•HCl obtained had a purity of 99% (5-chloro-2-methyl-3-isothiazolone/2-methyl-3-isothiazolone ratio of 3.9:1).

Following the procedure of Step 2 of Example 1, the isothiazolone•HCl salt was neutralized with ammonia to produce the free base isothiazolone in >99% purity and a 5-chloro-2-methyl-3-isothiazolone/2-methyl-3-isothiazolone ratio of 4.7:1 (<0.5% NH$_4$Cl).

EXAMPLE 6

Preparation of a 4:1 Mixture of 5-Chloro-2-Methyl-3-Isothiazolone/2-Methyl-3-Isothiazolone This example illustrates the process of the invention using ethyl acetate as the solvent in which only the chlorination/cyclization step was carried out, and in which the neutralization step using anhydrous ammonia was carried out in a mixture of a glycol and ethyl acetate as cosolvents.

The isothiazolone⅓HCl obtained had a purity of 98.3% and the 5-chloro-2-methyl-3-isothiazolone/2-methyl-3-isothiazolone ratio was 4:1.

Step 2: Neutralization of the Isothiazolone•HCl Salt

The isothiazolone•HCl wet cake (68.4 g) was reslurried in 126.6 g of ethyl acetate and 85.8 g of dipropylene glycol (DPG). The stirred slurry was then neutralized by passing ammonia gas through the mixture until free ammonia was detected in the head space (5.5 g of ammonia were required for neutralization). The resultant slurry of free base isothiazolone and ammonium chloride was then filtered and washed thoroughly with fresh ethyl acetate.

Step 3: Solvent Strip

The filtrate and the ethyl acetate washings were combined and to this was added 12.1 g triethyl orthoformate stabilizer. Ethyl acetate was then stripped off from this mixture at 50° C./20 to 5 mm Hg to give 132.3 g of a DPG liquid mixture containing 26.4% 5-chloro-2-methyl-3-isothiazolone, 6.6% 2-methyl-3-isothiazolone (4/1 ratio), <0.5% NH$_4$Cl.

Step 4: Formulation of 5-chloro-2-methyl-3-isothiazolone/2-methyl-3-isothiazolone in DPG.

The above solution was further diluted by adding 150.5 g of DPG and filtered to give a final formulation of 15.2% 5-chloro-2-methyl-3-isothiazolone/2-methyl-3-isothiazolone in DPG.

EXAMPLE 7

Preparation of 2-Octyl-3-Isothiazolone

This example illustrates the process of the invention using butyl acetate as the solvent in which both the chlorination/cyclization and neutralization are carried out, and anhydrous ammonia used as the neutralizing agent.

Step 1: Chlorination of N-Octyl-3-Mercaptopropionamide (OMPA)

A 1-liter jacketed kettle with a bottom take-off was equipped with an overhead agitator, a thermometer, a chlorine inlet, an inlet for a 28% solution of OMPA in butyl acetate, and a condenser connected to a caustic scrubber. To this kettle was charged butyl acetate. To the heel of butyl acetate were co-fed chlorine and the 28% OMPA solution over a 1-2 hour period while maintaining good mixing and temperature control. The resultant chlorination slurry of 2-octyl-3-isothiazolone•HCl was filtered to isolate the 2-octyl-3-isothiazolone•HCl cake. The 2-octyl-3-isothiazolone•HCl cake was washed thoroughly with butyl acetate to yield a highly pure 2-octyl-3-isothiazolone•HCl salt. An aliquot of 2-octyl-3-isothiazolone•HCl was dried and analyzed by GC (gas chromatography) for 2-octyl-3-isothiazolone and by potentiometric titration for HCl, which were 85.3% and 14.5%, respectively, bringing the total 2-octyl-3-isothiazolone•HCl purity to 99.8%.

Step 2: Neutralization of the 2-Octyl-3-Isothiazolone•HCl Salt

The 2-octyl-3-isothiazolone•HCl salt is reslurried in fresh butyl acetate (25% solids) and anhydrous ammonia is passed gradually through the slurry (maintained at 10°-22° C.) until free ammonia can be detected in the head space of the container by either wet litmus indicator paper or by an ammonia gas sensing probe. The resultant slurry of free base 2-octyl-3-isothiazolone and ammonium chloride is then filtered on a vacuum Buchner funnel and the filter cake is thoroughly washed with fresh butyl acetate.

Step 3: Solvent Strip

The filtrate and the butyl acetate washings are combined and stripped under reduced pressure to yield high purity (>99%) free base 2-octyl-3-isothiazolone product, <0.5% NH$_4$Cl.

Step 4: Formulation of 2-Octyl-3-Isothiazolone in Propylene Glycol

2-Octyl-3-isothiazolone (266 g) was dissolved in 1,2-propylene glycol (312 g) to give a 46% active ingredient solution. This formulation may be added to a commercial acrylic latex paint formulation, such that the paint will exhibit good storage stability in the can against bactericidal attack and will exhibit excellent resistance to mildew upon application to exterior surfaces.

EXAMPLE 8

Partial Neutralization of Isothiazolone•HCl Salt Mixture with Ammonia

This example describes the process of obtaining a mixture of the two isothiazolones in different ratios than they were present in the initial isothiazolone•HCl mixture.

A 95 g mixture of 5-chloro-2-methyl-3-isothiazolone•HCl and 2-methyl-3-isothiazolone•HCl (in 75.4:24.6 ratio) in 400 g ethyl acetate was partially neutralized at 10° C., using 95% of theoretical ammonia (6.2 g) needed to fully neutralize 5-chloro-2-methyl-3-isothiazolone•HCl. The resultant slurry, containing ammonium chloride and the isothiazolone•HCl salts mixture as solids and free base isothiazolone in solution was filtered on a vacuum Buchner funnel and the cake was washed with ethyl acetate.

The combined filtrate was stripped under vacuum (50° C./20 mm Hg) to give 55.3 g of a free base containing essentially 5-chloro-2-methyl-3-isothiazolone (96.1%) with only a small amount of 2-methyl-3-isothiazolone (1.1%).

The above wet cake of NH₄Cl/isothiazolone•HCl salts mixture was reslurried in 275 g ethyl acetate and was neutralized completely. It adsorbed 2.8 g NH₃ before NH₃ was detected in the head space. The resultant slurry was filtered and washed on a vacuum Buchner funnel. The filtrate on stripping in vacuum at 50° C./20 mm Hg) provided 23.9 g of a free base mixture containing 5-chloro-2-methyl-3-isothiazolone and 2-methyl-3-isothiazolone in a 25:75 ratio.

COMPARATIVE EXAMPLES EXAMPLES 9 and 10

Examples 9 and 10 illustrate the use of prior art practices with triethylamine (TEA) and pyridine (PYR) as neutralizing agents. Final product purity was lower when these organic amines were used, resulting in 2% or more amine•HCl salt (TEA•HCl or PYR•HCl) impurity being present compared to <0.5% ammonium chloride impurity in Examples 1–7.

EXAMPLE 9 (COMPARATIVE)

Preparation of a 4/1 Mixture of 5-Chloro-2-Methyl-3-Isothiazolone/2-Methyl-3-Isothiazolone Using Triethylamine (TEA)

A sample of isothiazolone•HCl wet cake (83.2 g) obtained following the procedure of Step 1 of Example 6 was reslurried in 383.5 g of ethyl acetate and 43 g of TEA was added dropwise to a stirred slurry of the isothiazolone•HCl wet cake while maintaining the temperature at 8°–12° C. At the end of the neutralization, the resultant slurry was allowed to warm to 23° C. and then filtered on a Buchner funnel. The solid TEA•HCl was washed with 300 g of ethyl acetate. The filtrate and washings were combined and the solvent was stripped off at 50° C. at 20 to 5 mm Hg to give 57.0 g of free base isothiazolone, containing 78.3% 5-chloro-2-methyl-3-isothiazolone/19.8% 2-methyl-3-isothiazolone/2.0% TEA•HCl.

EXAMPLE 10 (COMPARATIVE)

Preparation of a 4/1 Mixture of 5-Chloro-2-Methyl-3-Isothiazolone/2-Methyl-3-Isothiazolone using Pyridine (PYR)

A sample of isothiazolone•HCl wet cake (74.4 g) obtained according to Step 1 of Example 6 was reslurried in 410 g of ethyl acetate and 29.3 g of PYR was added dropwise to a stirred slurry of the isothiazolone•HCl wet cake while maintaining the temperature at 10° C. At the end of the neutralization, the resultant slurry was allowed to warm to 25° C. and was divided into two equal portions. One portion of the resultant slurry (246 g) was then filtered on a Buchner funnel. The solid PYR•HCl was washed with 250 g of ethyl acetate. The filtrate and washings were combined and the solvent was stripped off at 50° C. at 20 to 5 mm Hg to give 26.2 g of free base isothiazolone, containing 77.6% 5-chloro-2-methyl-3-isothiazolone/19.4% 2-methyl-3-isothiazolone/2.5% PYR•HCl. The second portion of the resultant slurry (244 g) was then treated with an additional 4.4 g of PYR and then filtered on a Buchner funnel. The solid PYR•HCl was washed with 250 g of ethyl acetate. The filtrate and washings were combined and the solvent was stripped off at 50° C. at 20 to 5 mm Hg to give 25.0 g of free base isothiazolone, containing 74.3% 5-chloro-2-methyl-3-isothiazolone/20.0% 2-methyl-3isothiazolone/4.4% PYR•HCl.

We claim:

1. A process for preparing a substantially water free 3-isothiazolone of the formula

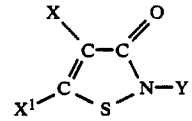

wherein

Y is selected from the group consisting of alkyl or hydroxy-or halogen-substituted alkyl of 1 to 10 carbon atoms; unsubstituted or halogen-substituted alkenyl or alkynyl of 2 to 10 carbon atoms; benzyl; 4-methoxybenzyl; 4-chlorobenzyl; phenethyl; 2-(4-chlorophenyl)ethyl; and 4-phenylbutyl;

X is hydrogen or a ($C_1$–$C_2$) alkyl; and $X^1$ is hydrogen, chlorine, or a ($C_1$–$C_2$) alkyl; comprising (a) reacting in the presence of an organic solvent selected from the group consisting of alcohol, glycol, glycol ether, acetate ester, aliphatic hydrocarbon, chlorinated aliphatic hydrocarbon, aromatic hydrocarbon, and chlorinated aromatic hydrocarbon solvents (i) anhydrous ammonia with (ii) an isothiazolone salt of the formula

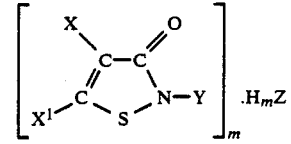

wherein

Z is chlorine, bromine, sulfate or fluorosulfonate;

m is 1 when Z is chlorine, bromine or fluorosulfonate, and m is 2 when Z is sulfate;

using the stochiometric amount or less than the stochiometric amount of anhydrous ammonia necessary to neutralize said salt; and (b) separating the resultant $(NH_4)_mZ$ from the resultant free base isothiazolone;

(c) said resultant free base isothiazolone containing less than about 0.5% $(NH_4)_mZ$ based on weight of isothiazolone.

2. Process according to claim 1 wherein said solvent is selected from the group consisting of ($C_1$–$C_5$)alkyl alcohol, ($C_2$–$C_8$)alkylene glycol, ($C_3$–$C_{10}$)alkylene glycol ether, ($C_6$)aromatic hydrocarbon, ($C_1$–$C_2$)alkyl-substituted aromatic hydrocarbon, chloro-substituted ($C_6$)aromatic hydrocarbon, chlorosubstituted ($C_1$–$C_2$)alkyl-substituted aromatic hydrocarbon, ($C_6$–$C_8$)alkane, chloro-substituted($C_1$–$C_3$)alkane, and ($C_1$–$C_4$)alkyl ester of acetic acid.

3. Process according to claim 1 wherein the solvent is selected from the group consisting of ethylene glycol, propylene glycol, 1,3-butanediol, dipropylene glycol, ethylene glycol butyl ether, toluene, monochlorobenzene, heptane, dichloromethane, 1,2-dichloroethane, ethyl acetate, and butyl acetate.

4. Process according to claim 1 wherein said salt is dissolved or suspended in organic solvent and the head space above the resultant solution or suspension is monitored during the reaction so as to determine when a sufficient amount of ammonia has been added.

5. Process according to claim 1 wherein the Y substituent is $(C_1-C_8)$alkyl.

6. Process according to claim 5 wherein Y is n-octyl, $X^1$ is hydrogen and X is hydrogen.

7. Process according to claim 5 wherein Y is methyl, $X^1$ is hydrogen and X is hydrogen.

8. Process according to claim 5 wherein Y is methyl, $X^1$ is chloro, and X is hydrogen.

9. Process according to claim 1 wherein said resultant free base isothiazolone is a mixture of 5-chloro-2-methyl-3-isothiazolone and 2-methyl-3-isothiazolone.

10. Process according to claim 9 wherein said 5-chloro-2-methyl-3-isothiazolone and 2-methyl-3-isothiazolone are in a ratio of about 92:8 to 3:97.

11. Process according to claim 1 wherein said resultant free base isothiazolone contains less than about 0.1% $(NH_4)_mZ$ based on weight of isothiazolone.

12. Process according to claim 1 wherein said isothiazolone contains less than about 0.1% water and less than about 0.1% $(NH_4)_mZ$ based on weight of isothiazolone.

13. Process according to claim 1 wherein m is 1 and Z is chlorine or bromine.

* * * * *